United States Patent [19]

Bergfeld et al.

[11] Patent Number: 6,075,153
[45] Date of Patent: Jun. 13, 2000

[54] PROCESS FOR THE PREPARATION OF GAMMA-BUTYROLACTONE AND THE USE THEREOF

[75] Inventors: Manfred J. Bergfeld, Erlenbach-Mechenhard; Kurt Uihlein, Grossheubach, both of Germany

[73] Assignee: Akzo Nobel NV, Arnhem, Netherlands

[21] Appl. No.: 09/051,542

[22] PCT Filed: Dec. 7, 1996

[86] PCT No.: PCT/EP96/05486

§ 371 Date: Apr. 13, 1998

§ 102(e) Date: Apr. 13, 1998

[87] PCT Pub. No.: WO97/24346

PCT Pub. Date: Jul. 10, 1997

[30] Foreign Application Priority Data

Dec. 27, 1995 [DE] Germany ............... 195 48 818

[51] Int. Cl.[7] .................................. C07D 307/26
[52] U.S. Cl. .............................................. 549/325
[58] Field of Search ....................... 549/326, 325

[56] References Cited

U.S. PATENT DOCUMENTS

| | | | |
|---|---|---|---|
| 3,065,243 | 11/1962 | Dunlop et al. | 260/343.6 |
| 4,001,282 | 1/1977 | Miller . | |
| 4,006,165 | 2/1977 | Micholczyk et al. | 260/343.6 |
| 5,347,021 | 9/1994 | Taylor et al. | 549/325 |
| 5,536,849 | 7/1996 | Bergfeld et al. . | |

FOREIGN PATENT DOCUMENTS

| | | |
|---|---|---|
| 840452 | 4/1970 | Canada . |
| 638565 | 2/1995 | European Pat. Off. . |
| 2404493 | of 0000 | Germany . |
| WO 91/16132 | 10/1991 | WIPO . |
| WO 97/24346 | 7/1997 | WIPO . |

OTHER PUBLICATIONS

Chemical Abstracts, vol. 119, No. 21, (1993).
Chemical Abstracts, vol. 118, No. 5, (1993).
B. Elvers et al., ed., "2–Pyrrolidone", *Ullman's Encyclopdia of Industrial Chemistry*, vol. A22, pp. 457–459, (1993).
Chemical abstracts, vol. 82 No. 21, 139947a, May 1975.

*Primary Examiner*—Amelia Owens
*Attorney, Agent, or Firm*—Oliff & Berridge, PLC

[57] ABSTRACT

A process for manufacturing gamma-butyrolactone by the catalytic hydrogenation of maleic anhydride, succinic anhydride or their acids in the vapor phase in the presence of catalysts based on copper oxide and aluminum oxide in reduced form is described. The process is characterized in that a catalyst is employed to conduct the reaction which is formed on the basis of 50 to 95% by weight copper oxide, 3 to 30% by weight aluminum oxide and 0 to 25% by weight of a binder. Preferably the catalyst is formed on the basis of 83.5 to 85.5% by weight copper oxide, 9 to 11% by weight aluminum oxide, and 4.5 to 6.5% by weight graphite. The reaction mixture obtained can be used directly without separating off the water, e.g. for manufacturing N-methylpyrrolidone.

20 Claims, No Drawings

PROCESS FOR THE PREPARATION OF GAMMA-BUTYROLACTONE AND THE USE THEREOF

FIELD OF THE INVENTION

The invention relates to a process for manufacturing gamma-butyrolactone by catalytic hydrogenation of maleic anhydride, succinic anhydride or their acids in the vapor phase and its use for manufacturing pyrrolidones and N-alkylpyrrolidones.

BACKGROUND

Gamma-butyrolactone is an important chemical significance as the basis for a large number of syntheses. For instance, it plays a role in the manufacture of butyric acid and its derivatives, 1,4-butanediol, tetrahydrofurane, N-methylpyrrolidone, polyvinylpyrrolidone, methionine and so forth. Gamma-butyrolactone is also an important solvent among other things for acrylates and styrol-based polymers. It can additionally be employed among other things in the manufacture of synthetic fibers.

A series of manufacturing processes start from maleic anhydride or derivatives such as maleic acid, succinic anhydride or maleate, which are subjected to hydrogenation. Hydrogenation is usually conducted in the vapor phase and in the presence of catalysts. In the patent literature a large number of catalysts are described for this reaction. For example, U.S. Pat. No. 3,065,243 mentions a process in which copper chromite acts as a catalyst. As can be gathered from the description and the examples in this patent specification, large quantities of succinic anhydride are still produced in this conversion which must be recirculated.

There has been no lack of attempts to develop catalysts to improve the yield and the selectivity. Another goal of the experimentation was to improve the lifetime of the catalysts since their useful lifetimes in continuous operation are too short: the catalyst deactivates too soon.

Thus, the Canadian patent specification 840 452 describes more advanced catalysts formed on the basis of copper/zinc. These can be processed together with asbestos into suitable catalyst particles. Neither the catalyst claimed in this Canadian patent specification nor the comparatively produced copper chromite-asbestos catalyst can yet fulfill all demands made on a good catalyst for the manufacture of gamma-butyrolactone.

DE-OS 24 04 493 describes a process in which the hydrogenation is performed in the presence of water vapor. This is intended to reduce the coking of the catalyst. One disadvantage of this process is the fact that additional water is introduced, although water is produced as a by-product in any case, which makes this process more expensive.

Other copper chromite-based catalysts are described for example in U.S. Pat. No. 4,006,165, where this catalyst also has to contain nickel. These catalysts can be applied to aluminum oxide or silica such as kieselgur or be produced by mixing with these substances.

EP-A1-0 638 565 describes a process in which gamma-butyrolactone is produced by catalytic hydrogenation of maleic anhydride in the vapor phase in the presence of catalysts based on copper chromite in reduced form. Although high selectivity and a good yield are achieved with the uniform, i.e. homogeneous catalyst based on the three components copper oxide, chromium oxide and silicon di-oxide, it appeared that the long-term capacity of the catalyst still leaves a lot to be desired.

U.S. Pat. No. 5,347,021 describes a process for manufacturing gamma-butyrolactone in which hydrogen and maleic anhydride are converted in the presence of a catalyst, again in the vapor phase. The catalyst is formed on the basis of the components copper oxide, zinc oxide, aluminum oxide and graphite. Although this process operates with comparatively good selectivity and a good yield, the catalyst has to be reactivated after this process has been running for about 100 hours.

Although a large number of catalysts for converting hydrogen and maleic anhydride into gamma-butyrolactone have already been described, there is still the need for catalysts with which this conversion can be conducted in a better, more advantageous manner.

SUMMARY OF THE INVENTION

The object of the invention is thus to make available a process for the manufacture of gamma-butyrolactone by the hydrogenation of maleic anhydride, succinic anhydride and their acids in the vapor phase in the presence of a catalyst which works with high yields, which possesses excellent selectivity, which can work both under high pressure and under normal or below atmospheric pressure, which is economical, which is flexible and which in particular offers advantages in terms of the isolation of the reaction product and the return of certain components into the cycle and which can also be operated in such a manner that recycling of succinic anhydride, which may be produced as an intermediate stage, is not necessary.

It is a further object of the invention to make available a process which can be operated over long periods of time without causing the catalyst to deactivate.

This task is solved by a process for manufacturing gamma-butyrolactone by the catalytic hydrogenation of maleic anhydride, succinic anhydride or their acids in the vapor phase in the presence of catalysts based on copper oxide and aluminum oxide in reduced form. A catalyst is used to conduct the reaction which is formed on the basis of 50 to 95% by weight copper oxide, 3 to 30% by weight aluminum oxide and 0 to 25% by weight of a binder. Preferably the catalyst used is formed on the basis of 80 to 90% by weight copper oxide, 5 to 15% by weight aluminum oxide, the difference to 100% by weight consisting of a binder. Graphite and silica gel are particularly suitable as binders. An especially advantageous catalyst for the process is formed on the basis of 83.5 to 85.5% by weight copper oxide, 9 to 11% by weight aluminum oxide, and 4.5 to 6.5% by weight graphite. It is advantageous for the catalyst to have a uniform structure, i.e. to be homogeneous. The catalyst can also be applied to a carrier. The hydrogenation can also be conducted in the presence of an inert gas, preferably nitrogen, acting as a diluent. Apart from nitrogen, the familiar noble gases such as argon, krypton, helium or a mixture of these together or with nitrogen can be used.

It is obvious that before its use in the reaction the catalyst on the basis of the three components is reduced in a manner which is well known per se. Preferably the reduction is conducted in the reactor itself.

For example, the reduction can be conducted in the following way: the catalyst which is present in the form of a catalyst bed is heated to 150° C. in the reactor in a stream of nitrogen. At this temperature hydrogen is slowly added up to an input concentration of up to 8% by volume whereby the temperature in the catalyst bed should not be increased by more than 25° C.

After the dissipation of the reaction heat the hydrogen concentration is increased to 80–100% by reducing the nitrogen stream and the temperature is raised to 280° C. The temperature is maintained for 12 hours under a stream of $H_2$. This process is generally termed follow-up reaction.

Naturally, the reduction can be conducted in other ways, for example as described in U.S. Pat. No. 3,065,243 in column 2, lines 54 to 66.

In the scope of the invention a uniform catalyst is taken to mean that the components are so thoroughly joined to one another that the catalyst has a uniform structure, i.e. it is essentially homogeneous and does not display any greater heterogeneous, dissimilarly structured components.

The catalyst can then be immediately introduced into the reactor and after suitable reduction be employed for the reaction.

The hydrogenation of maleic anhydride, i.e. the reaction of maleic anhydride with hydrogen is conducted in the vapor phase, i.e. at higher temperatures, e.g. in the range of about 100–400° C., the preferable range being about 260–320° C.

The vaporous maleic anhydride can itself be introduced into the reaction chamber by heating and converting into the vapor phase and suitable dosing. However, it is also possible to bring into the reactor the required amount of maleic anhydride vapors by means of the hydrogen stream which must be dosed. This can naturally also be effected by the inert gas such as nitrogen where this is also employed.

The molar ratio of maleic anhydride to hydrogen can vary over a wide range in the stream of the starting products. For instance it may be between 1:20 and 1:250. The preferable range is 1:40 to 1:100.

The reaction can be conducted both under normal pressure and partial vacuum or high pressure such as 0.1 to 10 bar.

In the scope of the invention inert gas signifies a substance which does not participate in the conversion as a reactant or reaction product and itself does not alter as a result of a reaction.

By means of using an inert gas as a diluent it is possible to influence the reaction positively. The ratio of inert gas, preferably including nitrogen, but which can also be a noble gas or carbon dioxide, or a mixture of these gases, to hydrogen can equally vary over a wide range. It is obvious that, depending on the other reaction conditions selected, the dilution is limited to the amount at which the proportion of the diluent is so large that too little hydrogen is present and the yield relative to maleic anhydride is reduced sharply. This limit can be determined by a few simple experiments which can be accomplished by one averagely skilled in the art.

It is possible to influence the reaction by varying quite different process parameters. For example, the residence time can be altered, which can be effected by setting different dosing speeds, but which can also be accomplished by increasing the reaction distance, for example by using a longer reaction tube suitably filled with catalyst. In order to accelerate the dissipation of the reaction heat the catalyst may be diluted in whole or part with a material with sufficient thermal conductivity and which is inert in the reaction medium. For this purpose e.g. steel spheres, steatite etc. are suitable.

The reaction can be controlled in such a way that the succinic anhydride produced as an intermediate stage is no longer present at the end of the reactor and thus no longer has to be recirculated. On the other hand, if required, the reaction can be controlled in such a way that succinic anhydride is still present in the reaction products outputted in larger or smaller amounts and then either further processed alone after being separated or recirculated.

The gamma-butyrolactone and the water formed are separated in a process which is well known per se.

It was a complete surprise to find that the use of the catalyst according to the invention causes both high selectivity and a high yield. The advantages of the catalyst employed according to the invention are not only apparent when working with or without diluents, they are also apparent when the molar ratios of the reactants are altered and when the temperature is varied. Thus, in the manufacture of gamma-butyrolactone by reduction of maleic anhydride by means of hydrogen, this catalyst can be used under the most varied process conditions to great advantage.

It was equally most surprising to discover that the use of the catalyst according to the invention allows for a process with a very long lifetime of the catalyst without deactivation occurring. Thus it is not necessary to renew or reactivate the catalyst after a short time of usage, which would lead to interruptions and would mean considerable expense.

A particular advantage is the fact that in the process according to the invention the gamma-butyrolactone formed can be employed directly, without separating off the water produced, in the manufacture of pyrrolidone and N-alkylpyrrolidones in the liquid phase under high pressure, particularly in the manufacture of N-methylpyrrolidone by the addition of methylamine.

Here, the classical amination process as described for instance in Ullmann's Encyclopedia of Industrial Chemistry, 5th revised edition, volume A22, pages 457–459 or in JP 49-20585, can be employed.

The invention will be described in more detail with the aid of the following examples:

DETAILED DESCRIPTION OF PREFERRED EMBODIMENTS

Example 1

Atmospheric Pressure without Hydrogen Recycling)

A catalyst composed of 77% copper oxide (CuO), 9% aluminum oxide ($Al_2O_3$), 5% graphite and 9% volatile components, especially water of hydration, which can be obtained from Mallinckrodt Chemical GmbH, D 53761 Hennef/Sieg, is first separated from its volatile components and reduced. The reduction of the catalyst is effected as follows:

The catalyst is heated at 150° C. in a stream of nitrogen. At this temperature hydrogen is slowly fed in up to an input concentration of up to 8% by volume, whereby the temperature increase of the packing is maintained at below 25° C. After the reaction heat has dissipated the hydrogen content is increased from 80% to 100% and the temperature raised to up to 280° C. The temperature is maintained for two hours under a stream of hydrogen (follow-up reaction).

Conducting the conversion

After this the desired quantity of maleic anhydride and hydrogen in gaseous form is fed in, i.e. 1 mol per hour hydrogen and 0.01 mol per hour maleic anhydride. The temperature of the heating is set to 265° C., whereby a hotspot at 7° C. is noticed. The yield was 98% with a conversion of 100%.

Example 2

Continuous Process Under Pressure with Hydrogen Recycling

In a stainless steel tube reactor with an inner diameter of 30 mm and a length of 1.2 m, 660 g catalyst as described in Example 1 is introduced without being crushed. 160 g of said 660 g of catalyst are mixed with 160 g of an inert material consisting of steel spheres in order to reduce the temperature in the range of the hotspot. This mixture forms the upper part of the catalyst packing. The heat is drawn off by means of a heat carrier oil which flows through the double shell of the reactor tube. The hydrogen employed for the hydrogenation is recycled after the products have been condensed (condensation at 25° C.). The condensed products are immediately subjected to analysis. About 10% of the hydrogen required for the conversion per se is removed in order to reduce the concentration of byproducts in the circulating gas. The pressure is 6 bar absolute.

In this process a hydrogen stream of 1000 nl/h through the reactor is set following reduction, where nl is norm liter. 60 g/h maleic anhydride is fed in. The freshly fed in hydrogen is 60 nl/h. The gas quantity removed is controlled via a pressure regulator. The addition of the maleic anhydride is effected in liquid form in a vaporization chamber upstream from the reactor itself. The gas quantity removed is controlled via a pressure regulator. The pressure is 6 bar.

At a heat carrier temperature of 277° C. and a maximum temperature measured in the reactor of 304° C. the yield remained constant at about 92% over a period of 1600 hours (see Table 1).

TABLE 1

| Time (h) | Yield (%) |
| --- | --- |
| 0 | 92.1 |
| 200 | 92.2 |
| 400 | 92.8 |
| 600 | 92.6 |
| 800 | 92.9 |
| 1100 | 93.3 |
| 1600 | 92.8 |

Example 3

Comparative Example

In order to determine the completely surprising superior reaction character of the catalyst of the invention, seven different catalysts on the basis of copper chromite are presented representing widely known copper chromite catalysts, while catalyst 8 is the catalyst of the invention. The catalysts are obtained by the precipitation of corresponding solutions. The composition of the catalysts employed is shown in Table 2, whereby the composition is that prior to reduction.

TABLE 2

| Composition (prior to reduction) | Catalyst No. |
| --- | --- |
| 2 CuO · $Cr_2O_3$* | 1 |
| Cu chromite (9.7% BaO) | 2 |
| 80% CuO, 20% $Cr_2O_3$ | 3 |
| 78% CuO, 20% $Cr_2O_3$, 2% $SiO_2$ | 4 |
| 42% CuO, 38% $Cr_2O_3$ | 5 |
| 33% CuO, 38% $Cr_2O_3$, 9% BaO | 6 |
| 76% CuO, 24% $Cr_2O_3$ | 7 |
| 84.6% CuO, 9.9% $Al_2O_3$, 5.5% graphite** | 8 |

*Commercial product E-113 T from Mallinckrodt
**Commercial product E-408 from Mallinckrodt The reduction was effected according to the following common process:

The catalyst bed which is already situated in the reactor provided is heated to 150° C. in a stream of nitrogen. At this temperature hydrogen is slowly added up to an input concentration of up to 8% by volume. The temperature increase of the packing should not be more than 25° C. (reduction step).

When the reaction heat has dissipated the hydrogen concentration is increased to 80–100% and the temperature is raised to 280° C. The temperature is maintained for 12 hours under a stream of $H_2$ (follow-up reduction).

Conducting the process:

The catalyst pellets are crushed and a fraction of 0.8 to 1.2 mm selected. These are placed in a quartz glass tube with an inner diameter of 1 cm and a length of 30 cm, which can be heated with silicon oil. After the reduction step described above has been conducted the experiment is begun. Hydrogen is dosed using a mass flow controller and the partial pressure of the maleic anhydride is set using a so-called saturator. This is effected by leading hydrogen and possibly nitrogen through the saturator, in which liquid maleic anhydride is located whereby a known partial pressure of maleic anhydride is set by means of the precisely fixed temperature. The mixture is introduced into the reactor via heated feed lines.

The catalysts were reduced as described above. In each case, the reactor was filled with 20 ml of the reduced catalyst and heated to a reaction temperature of 275° C. at a flow of 0.38 mol $N_2$/h and 2 mol $H_2$/h. Then the gas mixture was fed through the saturator and in this way a maleic anhydride mol flow of 0.02 mol/h was set. After a reaction time of 2 hours the product mixture was analyzed. The results are shown in the following Table 3.

TABLE 3

| Cat. No. | Yield (%) gamma-butyro-lactone | Yield (%) succinic anhydride | Conversion (%) maleic anhydride |
| --- | --- | --- | --- |
| 1 | 22.1 | 77.6 | 100 |
| 2 | 49.8 | 49.6 | 100 |
| 3 | 64.9 | 34.2 | 100 |
| 4 | 98.1 | — | 100 |
| 5 | 25.0 | 62 | 100 |
| 6 | 4.7 | 14.0 | 19.5 |
| 7 | 90.9 | 6.9 | 100 |
| 8 | 98.2 | 0 | 100 |

This illustrates the especial quality of catalysts 4 and 8, whereby it is particularly significant that the intermediate product succinic anhydride is also completely converted, otherwise technical problems with the crystallization of the succinic anhydride are often to be expected, such as blocking the tubing etc. The disadvantage of catalyst 4 compared to the catalyst according to the invention lies in its shorter lifetime in continuous operation, as the following example shows.

Example 4

Comparative Example

The unexpected advantage of the catalyst according to the invention over catalyst 4 is its essentially higher long-term stability. Within only a few hours catalyst 4 deactivated (see Table 4), whereas the catalyst according to the invention remained stable over a period of 1600 hours (see Table 1 and 4). The procedure, catalyst mass, reaction conditions and dilution are identical to those in Example 2. To facilitate comparison the results achieved with the catalyst according to the invention were shown again in Table 4.

TABLE 4

| Time [h] | Yield [%] | |
|---|---|---|
| | Catalyst No. 8 | Catalyst No. 4 |
| 0 | 92.1 | 91.1 |
| 20 | 92.5 | 89.2 |
| 40 | 92.7 | 85.4 |
| 100 | 92.4 | 82.6 |
| 200 | 92.2 | 73.1 |
| 400 | 92.8 | 56.4 |

Example 5

Manufacture of N-methylpyrrolidone 12.8 g of the reaction product mixture from Example 2 (0.11 mol gamma-butyrolactone) is mixed with 14 g 40% aqueous monomethylamine solution (0.19 mol monomethylamine) and put into a high-pressure autoclave. The mixture is heated to reaction temperature (290° C.), the pressure rising to 77 bar. After a reaction time of two hours more than 99% of the gamma-butyrolactone has been converted. The yield of N-methylpyrrolidone is 99.1% relative to gamma-butyro-lactone and 91.8% relative to maleic anhydride. The experiment is conducted according to the classical manufacturing process of NMP as described for example in JP 49-20585, but all reaction products from the first reaction stage such as water or butanol are still present in the educt mixture.

What is claimed is:

1. A process for manufacturing gamma-butyrolactone by catalytic hydrogenation of maleic anhydride, succinic anhydride or their acids in a vapor phase in the presence of a catalyst comprising copper oxide and aluminum oxide both in reduced form, wherein the catalyst is formed from of 50 to 95% by weight copper oxide, 3 to 30% by weight aluminum oxide and 0 to 25% by weight of a binder.

2. The process according to claim 1, wherein the catalyst is formed from of 80 to 90% by weight copper oxide, 5 to 15% by weight aluminum oxide, the difference to 100% by weight consisting of a binder.

3. The process according to claim 2, wherein the catalyst is formed from 83.5 to 85.5% by weight copper oxide, 9 to 11% by weight aluminum oxide and 4.5 to 6.5% by weight graphite.

4. The process according to claim 1, wherein the catalyst has a substantially uniform structure.

5. The process according to claim 1, wherein the catalyst is on a carrier.

6. The process according to claim 1, wherein the hydrogenation is conducted in the presence of pure hydrogen.

7. The process according to claim 1, wherein the hydrogenation is conducted in the presence of an inert gas acting as a diluent.

8. The process according to claim 7, wherein nitrogen is employed as the diluent.

9. The process according to claim 1, wherein the hydrogenation is conducted at a pressure between 0.1 and 10 bar.

10. The process according to claim 9, wherein the pressure is 4 to 7 bar.

11. The process according to claim 1, wherein the ratio of molar hydrogen in the vapor phase to maleic anhydride, succinic anhydride or their acids is between 20:1 and 250:1.

12. The process according to claim 11, wherein the ratio is between 40:1 and 100:1.

13. The process according to claim 1, characterized wherein the hydrogenation is performed in a temperature range of about 100 to 400° C.

14. The process according to claim 1, wherein excess hydrogen is recirculated after the reaction products have been condensed.

15. The process according to claim 14, wherein the condensation takes place at a temperature between 0° C. and 40° C.

16. The process according to claim 1, wherein the catalyst is prepared by reduction in a reactor.

17. The process according to claim 1, wherein the catalyst employed is diluted in whole or part with inert material.

18. The process according to claim 1, wherein the binder is graphite.

19. The process according to claim 1, wherein the binder is silica gel.

20. The process according to claim 13, wherein the hydrogenation is performed in a temperature range of 260 to 320° C.

* * * * *

UNITED STATES PATENT AND TRADEMARK OFFICE
CERTIFICATE OF CORRECTION

PATENT NO. : 6,075,153
DATED : June 13, 2000
INVENTOR(S) : Manfred J. Bergfeld and Kurt Uihlein It is certified that error appears in the above-identified patent and that said Letters Patent is hereby corrected as shown below:

Title Page,

Item [30],
After "195 48 818" insert -- .0 --;

Item [56],
Column 1,
U.S. PATENT DOCUMENTS, 4,006,165, change "Micholczyk" to -- Michalczyk --; and
Column 2,
FOREIGN PATENT DOCUMENTS, 2404493, change "of 0000" to -- 8/1974 --.

Column 1,
Line 14, change "an" to -- of --.

Column 3,
Line 17, after "hydrogen" insert -- , --.

Column 4,
Line 39, at the end of the line, delete ")".

Signed and Sealed this

Fourteenth Day of August, 2001

*Attest:*

*Attesting Officer*

NICHOLAS P. GODICI
*Acting Director of the United States Patent and Trademark Office*